(12) United States Patent
Gitter

(10) Patent No.: US 8,871,959 B2
(45) Date of Patent: Oct. 28, 2014

(54) METHOD FOR PRODUCING AN ALKYLENE OXIDE

(75) Inventor: Markus Gitter, Brussels (BE)

(73) Assignee: BASF SE, Ludwigshafen (DE)

( * ) Notice: Subject to any disclaimer, the term of this patent is extended or adjusted under 35 U.S.C. 154(b) by 832 days.

(21) Appl. No.: 13/122,999

(22) PCT Filed: Oct. 2, 2009

(86) PCT No.: PCT/EP2009/062804
§ 371 (c)(1),
(2), (4) Date: Apr. 7, 2011

(87) PCT Pub. No.: WO2010/040688
PCT Pub. Date: Apr. 15, 2010

(65) Prior Publication Data
US 2011/0196162 A1    Aug. 11, 2011

(30) Foreign Application Priority Data

Oct. 8, 2008 (EP) .................................. 08166057

(51) Int. Cl.
*C07D 303/00* (2006.01)
*C07D 301/03* (2006.01)
*C07D 301/10* (2006.01)

(52) U.S. Cl.
CPC ................. *C07D 301/10* (2013.01)
USPC ............ 549/536; 549/512; 549/534; 549/537

(58) Field of Classification Search
CPC ..................................................... C07D 301/10
USPC .......................................... 549/534, 536, 537
See application file for complete search history.

(56) References Cited

U.S. PATENT DOCUMENTS

| | | |
|---|---|---|
| 3,962,136 A | 6/1976 | Nielsen et al. |
| 4,007,135 A | 2/1977 | Hayden et al. |
| 4,010,115 A | 3/1977 | Nielsen et al. |
| 4,012,425 A | 3/1977 | Nielsen et al. |
| 4,051,068 A | 9/1977 | Rebsdat et al. |
| 4,123,385 A | 10/1978 | Rebsdat et al. |
| 4,134,926 A | 1/1979 | Tsao et al. |
| 4,177,169 A | 12/1979 | Rebsdat et al. |
| 4,324,699 A | 4/1982 | Mross et al. |
| 4,335,014 A | 6/1982 | Alfranseder et al. |
| 4,356,312 A | 10/1982 | Nielsen et al. |
| 4,389,338 A | 6/1983 | Mitsuhata et al. |
| 4,391,735 A | 7/1983 | Busse |
| 4,478,948 A | 10/1984 | Rebsdat et al. |
| 4,529,714 A | 7/1985 | Mross et al. |
| 4,732,918 A | 3/1988 | Lohmueller et al. |
| 4,774,222 A | 9/1988 | Rashkin |
| 5,011,809 A | 4/1991 | Herzog et al. |
| 6,624,116 B1 | 9/2003 | Bharadwaj et al. |

FOREIGN PATENT DOCUMENTS

| | | |
|---|---|---|
| CA | 992975 A1 | 7/1976 |
| CZ | 3150205 A1 | 8/1982 |
| DE | 2209392 A1 | 11/1972 |
| DE | 2300512 A1 | 7/1973 |
| DE | 2454972 A1 | 6/1975 |
| DE | 2521906 A1 | 12/1975 |
| DE | 2519599 B1 | 7/1976 |
| DE | 2611856 B1 | 9/1977 |
| DE | 2636680 A1 | 4/1978 |
| DE | 2649359 A1 | 5/1978 |
| DE | 2938245 A1 | 4/1981 |
| DE | 3321895 A1 | 12/1983 |
| DE | 3414717 A1 | 10/1985 |
| DE | 2560684 C2 | 10/1989 |
| EP | 0011356 A1 | 5/1980 |
| EP | 0014457 A2 | 8/1980 |
| EP | 0082609 A1 | 6/1983 |
| EP | 0085237 A1 | 8/1983 |
| EP | 0101008 A2 | 2/1984 |
| EP | 0172565 A2 | 2/1986 |
| EP | 0229465 A1 | 7/1987 |
| EP | 0266015 A1 | 5/1988 |
| EP | 0339748 A2 | 11/1989 |
| EP | 0357293 A1 | 3/1990 |
| EP | 0384312 A1 | 8/1990 |

OTHER PUBLICATIONS

"Myriad new surface alloys via electrolysis," Chem. Eng., 1967, pp. 100-102.
Arata, K., et al., "The Dehydration and Dehydrogenation of Ethanol Catalyzed by $TiO_2 ZrO_2$," Bull. Soc. Chem. Jpn., 1975, vol. 48, No. 11, pp. 3377-3378.
Banerjee, A. K., et al., "Selective Dehydration of Ethyl Alcohol to Ethylene By Vapour Phase Catalytic Process," Studies in Surface Science and Catalysis, Recent Advances in Basic and Applied Aspects of Industrial Catalysis, 1998, vol. 113, pp. 241-245.
Brunauer, S., et al., "Adsorption of Gases in Multimolecular Layers," J. Am. Chem. Soc., 1938, vol. 60, pp. 309-319.
Derouana, E. G., et al., "Elucidation of the Mechanism of Conversion of Methanol and Ethanol to Hydrocarbons on a New Type of Synthetic Zeolite," J. Catal., 1978, vol. 53, pp. 40-55.
Freidlin, L. Kh., et al., "An Investigation of the Effect of the Preparation Temperature of Boron Phosphate on Its Specific Surface, Acidity and Catalytic Activity in Dehydration of Alcohols," Kinetika i Kataliz, 1964, vol. 5, No. 2, pp. 347-350.
Klusáček, K., et al., "Multicomponent Diffusion of Gases in A Model Porous Catalyst During Methanol Dehydration," Chem. Eng. Sci., 1981. vol. 36, pp. 517-522.

(Continued)

*Primary Examiner* — T. Victor Oh
(74) *Attorney, Agent, or Firm* — Drinker Biddle & Reath LLP

(57) ABSTRACT

The present invention relates to a continuous process for producing an alkylene oxide by direct oxidation of an alkene with oxygen by reacting a mixture comprising alkene and oxygen in the presence of a silver-comprising catalyst for a run time $\Delta t(i)$, wherein during the oxidation, the catalyst is additionally contacted at least once with a further mixture comprising ethanol for a run time $\Delta t(ii)$, wherein the run time $\Delta t(i) > \Delta t(ii)$.

20 Claims, No Drawings

(56) References Cited

OTHER PUBLICATIONS

Mochida, I., et al., "Elimination Reactions on Solid Acid Catalysts," J. Catal., 1971, vol. 22, pp. 23-29.

Okuhara, T., et al., "The Important Role of the Bulk of 12-Tungustophosphoric Acid in the Catalytic Dehydration of Alcohols to Olefins," Chem. Lett., 1981, No. 3., pp. 391-394.

Pearson, D. E., et al., "Phosphoric Acid Systems. 2. Catalytic Conversion of Fermentation Ethanol to Ethylene," Ind. Eng. Chem. Prod. Res. Dev., 1981, vol. 20, pp. 734-740.

Ullmann's Encyclopedia of Industrial Chemistry, 5th ed., 1987, vol. A10, VCH Verlagsgesellschaft, Weinheim, pp. 117-135.

International Preliminary Report on Patentbility from the foreign counterpart application, International Application No. PCT/EP2009/062804.

METHOD FOR PRODUCING AN ALKYLENE OXIDE

CROSS-REFERENCE TO RELATED APPLICATIONS

This application is a national stage application (under 35 U.S.C. §371) of PCT/EP2009/062804, filed Oct. 2, 2009, which claims benefit of European application 08166057.3, filed Oct. 8, 2008.

BACKGROUND OF THE INVENTION

The present invention relates to a continuous process for producing an alkylene oxide by direct oxidation of an alkene with oxygen in the presence of a silver-comprising catalyst, wherein the process comprises an integrated treatment of the catalyst for increasing its activity and/or selectivity. The invention likewise relates to the use of such a process for regenerating a spent catalyst previously used for alkylene oxide production.

Alkylene oxides are important key chemicals which have varied uses. Various production processes for producing alkylene oxides are known in principle in the prior art. Alkylene oxides can be produced, for example, by reacting olefins with hydroperoxides, e.g. with hydrogen peroxide, or by direct oxidation with oxygen.

Ethylene oxide is produced industrially frequently by direct oxidation of ethylene with oxygen in the presence of silver-comprising catalysts. Frequently, supported catalysts are used onto which the catalytically active metallic silver was applied by means of a suitable process. As support material, use can be made in principle of various porous materials such as, e.g., activated carbon, dioxides of titanium, zirconium or silicon, or ceramic compositions or mixtures of these materials. Generally, α-aluminum oxide is used as support material.

In addition to silver and support material, these catalysts mostly comprise promoters for improving the catalytic properties. According to the prior art, for example alkali metal and/or alkaline earth metal compounds are applied to the support in small amounts. Some publications teach the use of transition metals such as tungsten or molybdenum. A particularly preferred promoter in the case of silver catalysts is rhenium. Catalysts which comprise rhenium and/or other transition metal promoters in combination with alkali metal and/or alkaline earth metal compounds are preferentially used in industry because of their high selectivity.

In the course of time a number of processes have been developed for the direct oxidation of alkenes, in particular ethylene, using various silver catalysts with the purpose of beneficially affecting the selectivity and/or activity. Selectivity is taken to mean the molar percentage of alkylene which reacts to form alkylene oxide. The activity is characterized by the alkylene oxide concentration at the reactor outlet under otherwise constant conditions, such as, for example, temperature, pressure, gas rate, catalyst rate. The higher the alkylene oxide concentration, the higher is the activity. The lower the temperature which is required to reach a certain alkylene oxide concentration, the higher is the activity. Owing to the large amounts of, for example, ethylene oxide which are produced in industrial processes by the direct oxidation process, any increase in selectivity or activity of a catalyst is of considerable economic importance. In addition to the activity, the service life of the catalyst is of enormous economic importance. The activity and/or selectivity of known catalysts decrease with advancing time of use, so that finally an economically unfavorable change of catalyst must proceed.

Processes for improving the activity and/or selectivity of spent silver catalysts are mostly based on post-treating or regenerating a spent catalyst. The post treatment comprises, for example, impregnating the spent catalyst with a solution comprising water, a water-miscible solvent and a cesium and/or rubidium compound. The catalyst which is impregnated in this manner is dried and the catalyst thus dried is then used again in the oxidation reaction. Such processes are described, for example, in DE 25 19 599, DE 26 11 856, DE 26 36 680, DE 26 49 359, EP 0 101 008 and DE 29 38 245. In the regeneration processes which are described in U.S. Pat. No. 4,529,714 or U.S. Pat. No. 4,391,735, the silver-comprising catalyst is treated in a very similar manner; but the regeneration solution here comprises additionally hydrazine and/or aliphatic or aromatic acids as additives.

However, the processes described have the disadvantage that the oxidation process must be interrupted for the entire period of treatment of the catalyst. A process in which activity and/or selectivity of the silver catalyst can be improved in situ by a suitable treatment at a given time during the running process appears to be advantageous. The expression "in situ", as used in the context of the invention, means a treatment of the catalyst is carried out during the running oxidation reaction without the oxidation process being interrupted.

An in situ regeneration process is described in U.S. Pat. No. 6,624,116. This document relates to a process for regenerating a catalyst which is used in an autothermal oxidation process for converting paraffin hydrocarbons to olefins. The regeneration is achieved by introducing a vaporizable compound of the metals of group 8b and/or by introducing a vaporizable promoter into the reactor together with the reaction mixture. Silver-comprising catalysts and processes for the direct oxidation of alkenes to alkylene oxides are not described in U.S. Pat. No. 6,624,116.

There was therefore the need for advantageous processes for producing alkylene oxides by direct oxidation of alkenes in the presence of silver-comprising catalysts in which the above described disadvantages, that is, for example, frequent production outage and/or losses of activity and/or selectivity during advancing period of use, are minimized. In addition, there was the need for an advantageous regeneration process for silver-comprising catalysts which are used in the direct oxidation of alkenes.

Surprisingly, it has now been found that the selectivity and activity are beneficially affected by an in-situ treatment of a silver-comprising catalyst with an ethanol-comprising mixture which is carried out during the production of an alkylene oxide by direct oxidation of an alkene with oxygen.

BRIEF SUMMARY OF THE INVENTION

Therefore, the present invention relates to a continuous process for producing an alkylene oxide by direct oxidation of an alkene with oxygen, which comprises (i) continuous contacting of a silver-comprising catalyst with a mixture G1 comprising the alkene and oxygen for a run time Δt(i);

(ii) contacting at least once the catalyst according to (i) during the continuous contacting according to (i) with an additional mixture G2 comprising ethanol for a run time Δt(ii), wherein Δt(i)>Δt(ii).

DETAILED DESCRIPTION OF THE INVENTION

The process according to the invention can in this case also be taken to mean a regeneration process for regenerating a silver-comprising catalyst which is used in the direct oxidation of alkenes to alkylene oxides, in which the regeneration of the catalyst is carried out in situ, that is as defined above, during the running oxidation reaction without the oxidation process being interrupted in this case.

Therefore the invention relates to the use of the abovementioned process for the in-situ regeneration of a silver-comprising catalyst.

The process according to the invention is particularly suitable for the direct oxidation of alkenes having 2 to 4 carbon atoms, in particular for the direct oxidation of ethylene or propene. Particularly preferably, the process is used for the direct oxidation of ethylene to ethylene oxide.

Accordingly, the present invention also relates to a process as described above, wherein the alkene is ethylene and the alkylene oxide is ethylene oxide. The invention likewise relates to the use of this process for the in-situ regeneration of a silver-comprising catalyst while this is being used for producing ethylene oxide.

Catalysts which can be used in the process according to the invention or which can be regenerated in situ by the process according to the invention are in principle all silver-comprising catalysts which are suitable for producing ethylene oxide from ethylene and oxygen. Preferably, the catalysts are supported catalysts, i.e. catalysts which comprise at least one inert support material. As support material, use can be made of, in principle, any porous material which is stable under the conditions of the direct oxidation according to the invention, for example activated carbon, aluminum oxides, dioxides of titanium, zirconium or silicon, silicon carbide or other ceramic compositions or suitable mixtures of these materials. Preferably, the catalyst comprises aluminum oxide, for example at least one alpha-, gamma- or theta-aluminum oxide, in particular an alpha-aluminum oxide.

Accordingly, the present invention also relates to a process as described above, wherein the silver-comprising catalyst comprises an inert support material, preferably alpha-aluminum oxide.

According to a preferred embodiment, the process is carried out using a catalyst which comprises as support material an alpha-aluminum oxide having a BET surface area determined as described by Brunauer et al., J. Am. Chem. Soc. 60, page 309 (1938) of 0.1 to 20 m$^2$/g, preferably 0.2 to 10 m$^2$/g, further preferably in the range from 0.3 to 5 m$^2$/g, further preferably in the range from 0.4 to 3 m$^2$/g, further preferably in the range from 0.5 to 2 m$^2$/g, and particularly preferably in the range from 0.7 to 1.2 m$^2$/g. In addition this alpha-aluminum oxide preferably has pore volumes in the range from 0.1 to 2.0 ml/g, preferably in the range from 0.2 to 1.2 ml/g, further preferably in the range from 0.4 to 1.0 ml/g, and particularly preferably in the range from 0.4 to 0.8 ml/g, measured by the process of mercury porosimetry as specified in DIN 66133 and exhibits a cold water absorption at 20° C. in the course of 5 min of 0.1 to 2.0 ml/g, preferably from 0.2 to 1.2 ml/g, further preferably from 0.4 to 1.0 ml/g, and particularly preferably in the range from 0.4 to 0.8 ml/g.

According to a further preferred embodiment, the alpha-aluminum oxide has a purity greater than 75%, preferably a purity greater than 80%, further preferably a purity greater than 85%, further preferably a purity greater than 90%, and very particularly preferably a purity greater than 98%.

The expression "alpha-aluminum oxide" in this case also comprises alpha-aluminum oxides which comprise further components, for example one or more compounds, preferably oxides of the elements selected from the group consisting of sodium, potassium, rubidium, cesium, magnesium, calcium, strontium, barium, silicon, iron, zirconium, and mixtures of one or more of these elements. For example, the alpha-aluminum oxide comprises one or more compounds selected from the group consisting of silicon dioxide, sodium oxide, iron(III) oxide, titanium dioxide, calcium oxide, zirconium oxide, potassium oxide and magnesium oxide.

Preferably, the inert support material is an alpha-aluminum oxide in a purity of at least 98%.

According to a further preferred embodiment, the alpha-aluminum oxide, which preferably has a purity of at least 98%, comprises less than 1% by weight of silicon dioxide. If the alpha-aluminum oxide comprises sodium oxide, it preferably comprises this in an amount from 0.01 to 0.5% by weight, preferably in an amount from 0.08 to 0.12% by weight, in each case based on the total weight of the inert support material. If the alpha-aluminum oxide comprises iron (III) oxide, it likewise comprises this preferably in an amount from 0.01 to 0.5% by weight, preferably in an amount from 0.08 to 0.12% by weight, in each case based on the total weight of the inert support material. If the alpha-aluminum oxide comprises titanium dioxide, it preferably comprises this in an amount of less than 0.5% by weight, preferably in an amount of less than 0.3% by weight, further preferably in an amount of less than 0.02% by weight, in each case based on the total weight of the inert support material. If the alpha-aluminum oxide comprises, for example, sodium oxide, it preferably comprises this in an amount from 0.01 to 0.5% by weight, preferably in an amount from 0.08 to 0.12% by weight, in each case based on the total weight of the inert support material. If the alpha-aluminum oxide comprises calcium oxide, it preferably comprises this in an amount from 0.01 to 0.5% by weight, preferably in an amount from 0.08 to 0.12% by weight, in each case based on the total weight of the inert support material. If the alpha-aluminum oxide comprises magnesium oxide, it preferably comprises this in an amount from 0.01 to 0.5% by weight, preferably in an amount from 0.08 to 0.12% by weight, in each case based on the total weight of the inert support material. If the alpha-aluminum oxide comprises potassium oxide, it preferably comprises this in an amount from 0.01 to 0.5% by weight, preferably in an amount from 0.08 to 0.12% by weight, in each case based on the total weight of the inert support material. Customarily, the inert support material comprises zirconium dioxide in an amount of less than 0.1% by weight, preferably less than 0.05% by weight, in each case based on the total weight of the inert support material. Use can be made of, for example, supports of the type SA5-61 from Saint-Gobain N or Pro or type 19/30 from CeramTec.

The geometric shape of the support particles is in principle optional. Expediently, the support particles have shapes which enable unhindered diffusion of the reaction gases to the outer and inner surfaces of the support particles which are coated with the catalytically active silver particles. Preferred support shapes are tablets, ropes, balls, lens- or egg-shaped bodies, particularly preferably ropes. Very particular preference is given to hollow ropes, perforated star ropes or perforated label ropes.

As regards the amount of silver, in the process according to the invention, preferably use is made of catalysts which comprise silver in an amount in the range from 10 to 30% by weight. Particular preference is given to catalysts which comprise silver in an amount in the range from 10 to 20% by weight, further preferably from 12 to 18% by weight, and particularly preferably from 13 to 16% by weight, in each case based on the total weight of the catalyst.

Accordingly, the present invention also relates to a process as described above, wherein the catalyst comprises silver in an amount of 10 to 30% by weight, based on the total weight of the catalyst.

In addition to silver, the catalysts used in the process according to the invention preferably comprise at least one promoter, for example six, five, four, three, two promoters, or 1 promoter. A "promoter", in the context of the invention, is taken to mean a component of the catalyst by which an improvement in one or more catalytic properties, for example selectivity, activity, conversion rate and/or yield or space-time yield is achieved compared with a catalyst which does not comprise the component. Preference is given to those compounds which are very largely chemically stable under the reaction conditions and do not catalyze unwanted reactions. As examples of promoter-doped silver catalysts which can be used in the process according to the invention, mention may be made of the silver catalysts which are described in DE-A 23 00 512, for example on page 4, line 5 to page 11, line 5, in DE-A 25 21 906, for example on page 2, line 12 to page 7, in EP-A 0 014 457, for example on page 4, line 14 to page 6, line 30, in DE-A 24 54 972, for example on page 3, 3rd paragraph and on page 5 to page 14, in EP-A 0 357 293, for example column 1, line 10 to line 24 and in columns 4 and 5, EP-A 0 011 356, for example on page 1, line 19 to page 2, line 14 and on pages 3 to 5, line 20, and also in EP-A 0 266 015, EP-A 0 172 565, EP A 0 085 237 and DE-A 25 60 684.

Accordingly the present invention also relates to a process as described above, wherein the catalyst additionally comprises at least one promoter. In addition, the invention relates to the use of this process for in-situ regeneration of a catalyst comprising silver and at least one promoter, while this catalyst is being used for producing an alkylene oxide.

As promoters, mention may be made of, in particular, hydroxides or salts of the alkali metals and alkaline earth metals, and also compounds of elements of the 6th and 7th subgroup of the Periodic Table of the Elements, in particular compounds of the elements tungsten, molybdenum and/or rhenium. Catalysts which are particularly suitable for the process are catalysts which comprise a promoter selected from the group consisting of Re, W, Mo, Rb, Li, K, Cs, Sr, Ba, Ca, S, P, B, In, Sn, Sb, Tl, Pb and Bi and mixtures of two or more thereof.

Accordingly, the present invention also relates to a process as described above, wherein the at least one promoter is selected from the group consisting of Re, W, Mo, Rb, Li, K, Cs, Sr, Ba, Ca, S, P, B, In, Sn, Sb, Tl, Pb and Bi and mixtures of two or more thereof.

The process is very particularly suitable for catalysts which comprise at least one promoter selected from the group consisting of Li, Cs, W, Mo, S and Re and mixtures of two or more thereof. According to a particularly preferred embodiment, the catalyst comprises as promoter at least lithium and sulfur.

The catalysts used in the process according to the invention are preferably produced by applying the active components to the inert support material, i.e. by applying silver and applying the at least one promoter. For this, in principle all impregnation and deposition processes of the prior art can be used, wherein these processes can comprise one or more impregnation and/or deposition stages and also one or more calcination stages. As examples, the production processes for silver catalysts may be mentioned as are disclosed in DE-A 23 00 512, for example on page 11, line 14 to page 21, line 4, and in the examples, in DE-A 25 21 906, for example on page 7 to page 14, line 4, in EPA 0 014 457, for example on page 4, line 1 to page 8, line 16 and in example 1 and 2, EP-A 0 011 356, for example on page 2, line 15 to page 6, line 13, in DE-A 24 54 972, for example on page 3, 3rd paragraph and on page 5 to page 14, in EP-A 0 357 293, for example in column 1, line 25 to column 4, line 17, and also in EP-A 0 384 312, DE-A 33 21 895, EP-A 0 229 465, DE-A 31 50 205, and EP-A 0 172 565. In the production of the catalyst, silver, preferably in the form of a silver compound which can be a salt or a silver complex, is applied to the above described inert support material. Preferably, the silver compound is applied in dissolved form, in particular dissolved in water. In order to obtain the silver compound in soluble form, to the silver compound, such as, for example, silver(I) oxide or silver(I) oxalate, there can additionally be added in a suitable manner a complexing agent such as ethanolamine, oxalic acid and/or ethylenediamine, which complexing agent can simultaneously also act as reducing agent. Particularly preferably, silver is applied in the form of a silver-amine compound, preferably a silver-ethylenediamine compound. The promoters are in addition preferably used in the form of their salts, for example the halides, in particular the fluorides, chlorides, carboxylates, nitrates, sulfates or sulfides, phosphates, cyanides, hydroxides, carbonates or the salts of heteropolyacids, in particular of heteropolyacids of the elements of subgroups 6 and 7 of the Periodic Table of the Elements, particularly preferably in the form of salts of heteropolyacids of tungsten, molybdenum and/or rhenium, in the deposition and/or impregnation process.

As catalysts which are preferably used in the process according to the invention, mention may be made by way of example of silver catalysts having a silver content of 10 to 30% by weight, based on the total weight of the catalyst, a content of lithium and/or cesium from 1 to 5000 ppm by weight, a content of tungsten and/or molybdenum from 1 to 5000 ppm by weight and a content of sulfur from 1 to 500 ppm by weight, in each case based on the total weight of the catalyst. In addition the catalyst optionally comprises rhenium in a content from 0 to 3000 ppm by weight, based on the total weight of the catalyst.

The above described catalysts can be contacted with mixture G1 according to (i) in principle under any conditions which are suitable for the direct oxidation.

Typically, the contacting proceeds in at least one reactor, wherein use can be made of reactors which are conventional in the prior art in the ethylene oxide production processes. For example, use can be made of externally cooled shell and tube reactors (cf. Ullmann's Encyclopedia of Industrial Chemistry; 5th ed.; vol. A10; pp. 117-135, 123-125; VCH Verlagsgesellschaft; Weinheim 1987) or else reactors having a loose catalyst bed and cooling tubes, for example the reactors described in DE-A 34 14 717, EP-A 0 082 609 and EP-A 0 339 748. Preferably, the contacting according to (ii) is carried out in at least one tubular reactor, preferably in a shell and tube reactor. The mixture G1 in this case is preferably fed in a gaseous state into the reactor and there brought into contact with the catalyst.

The mixture G1 which is fed in and comprises alkene, preferably ethylene, and oxygen, preferably comprises an alkene amount in the range from 10 to 80% by volume, preferably from 20 to 60% by volume, further preferably from 25 to 50% by volume, and very particularly preferably from 30 to 40% by volume, based on the total volume of G1. The oxygen content of the mixture G1 is expediently in a range in which no explosive gas mixtures occur. Preferably, G1 comprises an oxygen amount of at most 10% by volume, preferably an amount of at most 9% by volume, further preferably an amount of at most 8% by volume, and very particularly preferably an amount of at most 7% by volume, based on the total volume of G1.

Accordingly, the present invention also describes a process as explained above, wherein the mixture G1 comprises the alkene, preferably ethylene, in an amount in the range from 30 to 40% by volume, and oxygen in an amount of at most 7% by volume.

In addition to these components, the mixture G1 preferably comprises further components. According to a preferred embodiment, the present invention relates to a process as described above, wherein the mixture G1 comprises an inert gas. Inert gas is taken to mean those gases which behave very substantially in an inert manner under the reaction conditions of the present invention. In particular, the inert gas is selected from the group consisting of nitrogen, argon, methane, carbon monoxide, helium and mixtures of two or more thereof. In particular, the mixture G1, additionally to ethylene and oxygen, comprises methane. If the mixture G1 comprises methane, it preferably comprises this in an amount in the range from 10 to 80% by volume, preferably from 20 to 70% by volume, further preferably from 30 to 60% by volume, and very particularly preferably from 40 to 50% by volume, in each case based on the total volume of G1.

In addition, the mixture G1 can comprise steam. If the mixture G1 comprises steam, it preferably comprises this in an amount in the range from 0.05 to 5.0% by volume, preferably from 0.05 to 3.0% by volume, further preferably from 0.05 to 2.0% by volume, further preferably from 0.05 to 1.0% by volume, and very particularly preferably from 0.05 to 0.5% by volume, in each case based on the total volume of G1.

According to a particularly preferred embodiment, the mixture G1 comprises methane in an amount from 40 to 50% by volume, and steam in an amount from 0.05 to 0.5% by volume, in each case based on the total volume of G1.

As a further component, the mixture can comprise carbon dioxide. The carbon dioxide amount in the mixture G1 is generally less than 2.5% by volume, preferably less than 2% by volume, for example preferably in the range from 0 to 1.8% by volume, further preferably in the range from 0 to 1.5% by volume, further preferably in the range from 0 to 1.0% by volume, in each case based on the total volume of G1.

In addition the mixture G1 comprising ethylene and oxygen can comprise a halogen compound. The halogen is preferably chlorine, whereas preferred halogen compounds are organic halogen compounds, preferably halides of hydrocarbons having 1 to 10 carbon atoms. Suitable compounds are, for example, chlorinated aromatic compounds, e.g. chlorobenzene, dichlorobenzenes or chlorinated toluenes. Particularly preferably, the halogen compound is selected from the group consisting of ethyl chloride, 1,1-dichloroethane, 1,2-dichloroethane, methyl chloride, methylene chloride, vinyl chloride and mixtures of one or more of these compounds.

Accordingly, the present invention also relates to a process as described above, wherein the mixture G1 additionally comprises an organic halide, preferably an organic halide selected from the group consisting of ethyl chloride, methyl chloride, methylene chloride, vinyl chloride, 1,1-dichloroethane and 1,2-dichloroethane or mixtures of one or more of these compounds. Very particularly preferably, the mixture G1 comprises ethyl chloride.

The halogen compound, preferably the organic halide, is generally used in a concentration of 0.1 to 2000 ppm by volume, preferably in a concentration from 1 to 1000 ppm by volume, further preferably in a concentration from 0.5 to 100 ppm by volume, particularly preferably in an amount from 1 to 20 ppm by volume, in each case based on the total volume of the mixture G1. In this case the amount of ethyl chloride in the mixture G1 which is fed continuously into the reactor can vary during the run time $\Delta t(i)$. As required, the amount of ethyl chloride is adapted during the reaction. Customarily, the ethyl chloride concentration at the start of the run time $\Delta t(i)$ is lower than at the end of the run time $\Delta t(i)$, i.e. the ethyl chloride concentration is customarily increased in the course of contacting. This increase can proceed continuously or stepwise, wherein customarily a stepwise increase of the ethyl chloride concentration proceeds. Customarily, at the start of the run time $\Delta t(i)$ an amount of ethyl chloride is selected which is in the range from 1 to 4 ppm by volume, whereas the amount of ethyl chloride at the end of the run time $\Delta t(i)$ is customarily in the range from 4 to 20 ppm by volume, in each case based on the total volume of G1.

In addition to said components, the mixture G1 can additionally comprise a suitable nitrogen compound, for example nitrogen monoxide, nitrogen dioxide, $N_2O_4$, ammonia, nitromethane, nitroethane and/or $N_2O_3$, wherein nitrogen monoxide and/or nitrogen dioxide are particularly advantageous. The nitrogen compound is generally used in concentrations from 0.1 to about 2000 ppm by volume, preferably in the range from 0.1 to 2000 ppm by volume, further preferably in the range from 1 to 1000 ppm by volume, and particularly preferably in the range from 50 to 500 ppm by volume, in each case based on the total volume of G1.

Accordingly, the present invention also relates to a process as described above, wherein the mixture G1 additionally comprises a nitrogen compound, preferably nitrogen monoxide and/or nitrogen dioxide.

According to a particularly preferred embodiment, the mixture G1 comprises ethylene in an amount in the range from 30 to 40% by volume, oxygen in an amount of at most 78% by volume, steam in an amount in the range from 0.05 to 0.5% by volume, carbon dioxide in an amount in the range from 0.1 to 1.0% by volume, methane in an amount in the range from 40 to 50% by volume, and also ethyl chloride in an amount from 1 to 20 ppm by volume, in each case based on the total volume of the mixture G1.

The above described components of the gas mixture can if appropriate each comprise small amounts of impurities. Ethylene can be used, for example, in any purity stages which are suitable for the gas phase oxidation according to the invention. Suitable purity stages include, but are not limited to, "polymer grade" ethylene which typically has a purity of at least 99%, and "chemical grade" ethylene which has a lower purity of typically greater than 95%. The impurities in this case typically comprise especially ethane, propane and/or propene.

In the context of the invention, the ethylene can be provided in any suitable manner. Generally, the ethylene used in the process according to the invention originates from steam cracking processes, for example steam cracking of oil and/or naphtha or steam cracking of ethane which occurs as an accompanying gas in the extraction of petroleum or natural gas. Likewise, the ethylene can also originate from a catalytic, oxidative or autothermal dehydrogenation of ethane.

According to an alternative embodiment of the invention, use is made of ethylene which is obtained by dehydrating ethanol. Ethanol in turn can very easily be obtained by fermentation from sugar- or starch-comprising plants such as sugarcane, sugar beets, corn, rye, etc. Owing to the good availability of these renewable raw materials, inexpensive supply with ethanol and ethylene produced therefrom by catalytic dehydration is ensured in the long term.

Accordingly, the present invention also relates to a process as described above, additionally comprising (a) providing ethylene by dehydrating ethanol.

The dehydration of ethanol to give ethylene is a technology which is known per se and can be carried out as described in the literature listed hereinafter. Until the 1960s, the production of ethylene from ethanol on a small scale (2-10 kt/a) was quite widespread, see Chem. Eng. 1967, 100-102. At locations without access to hydrocarbons and with advantageous ethanol from biomass (in particular sugarcane), ethanol dehydration was pursued further, see Chem. Eng. 1981, 17. Temperature control is decisive for ethylene selectivity. At temperatures which are too low (<300° C.), diethyl ether is formed, and at temperatures which are too high (>400° C.) the fraction of acetaldehyde increases. For the industrial synthesis of ethylene which is described in U.S. Pat. No. 4,134,926 in a fluidized-bed reactor at temperatures between 400 and 480° C. in the presence of an $SiO_2/Al_2O_3$ cracking catalyst, yields of 99% and more are reported. As catalysts, use is generally made of oxidic catalysts, e.g. $Al_2O_3$, $ZrO_2$ (see Bull. Soc. Chem. Jpn. 1975, 48, 3377), salts such as sulfates (see J. Catal. 1971, 22, 23), phosphates (see Kinet. Katal. 1964, 5, 347), (hetero)polyphosphoric acids (see Chem. Lett. 1981, 391; Ind. Eng. Chem., Prod. Res. Dev. 1981, 20, 734), zeolites such as ZSM-5 (see J. Catal. 1978, 53, 40), ion exchange resins or else supported phosphoric acid. T. S. R. P. Rao and G. M. Dhar report, for a gamma-$Al_2O_3$ catalyst at 350° C., 375° C. and 400° C., not only 100% activity, but also 100% selectivity (Recent Advances in Basic and Applied Aspects of Industrial Catalysis, Studies in Surface Science and Catalysis 1998, Vol. 113, 241).

Ethanol can be dehydrated in principle by all the processes described in the prior art. Preferably, the dehydration proceeds in the presence of a catalyst comprising a zeolite of the type ZSM-5, or a catalyst comprising gamma-aluminum oxide. Preferably, the dehydration is carried out in a temperature range from 300° C. to 400° C. at atmospheric pressure. The feed gas in this case, further preferably, comprises gaseous ethanol. According to an alternative embodiment, a feed gas comprising a mixture of ethanol and at least one inert gas, preferably a mixture of nitrogen and ethanol, is used. "Comprising ethanol" in this context means that the ethanol can comprise the customary impurities present in ethanol such as, for example, methanol, propanol, acetaldehyde and/or acetic acid. "Comprising a mixture of ethanol and at least one inert gas" means, in addition, that the mixture can comprise the customary impurities present in ethanol and/or the customary impurities present in the at least one inert gas used, for example the customary impurities present in the nitrogen.

According to a preferred embodiment, the provision according to (a) comprises a purification of the mixture which comprises the ethylene obtained from the dehydration. Preferably, the purification proceeds by gas scrubbing and/or condensation, wherein residues of ethanol are absorbed or condensed out.

Preferably, at least a part of the ethylene which is obtained from the dehydration and which is, if appropriate, purified, is used as a component of the mixture G1 according to (i).

Accordingly, the present invention also relates to a process as described above, in addition comprising
(a) providing ethylene by dehydrating ethanol, wherein at least a part of the ethylene from (a) is used as a component of the mixture G1 according to (i).

The mixture G1 is contacted with the silver-comprising catalyst customarily at elevated temperature. Preference is given to temperatures in the range from 180° C. to 300° C., further preferably temperatures in the range from 185° C. to 290° C., further preferably temperatures in the range from 190° C. to 280° C., and particularly preferably temperatures in the range from 200° C. to 270° C. Accordingly, the present invention also relates to a process, as described above, wherein the contacting according to (i) proceeds at a temperature in the range from 180° C. to 300° C., preferably in the range from 200° C. to 270° C. Customarily, (i) is carried out at pressures in the range from 5 bar to 30 bar. Preferably, the contacting according to (i) proceeds at a pressure in the range from 5 bar to 25 bar, preferably at a pressure in the range from 10 bar to 20 bar, and particularly preferably at a pressure in the range from 14 bar to 20 bar. Accordingly, the present invention also relates to a process as described above, wherein the contacting according to (i) proceeds at a pressure in the range from 14 bar to 20 bar.

The gas hourly space velocity (GHSV) used in (i) is dependent on the type of the reactor selected, for example on the size/mean area of the reactor, and the form and size of the catalyst. Preferably, the GHSV is in the range from 800 to 10 000 per hour, preferably in the range from 2000 to 6000, further preferably in the range from 3000 to 6000, wherein the figure relates to the volume of the catalyst.

Accordingly, the present invention also relates to a process as described above, wherein the contacting according to (i) proceeds with a GHSV in the range from 3000 to 6000.

Typically, the contacting according to (i) is carried out for a run time $\Delta t(i)$ which is greater than 100 h. The run time $\Delta t(i)$ in this case is taken to mean the total run time of an oxidation process carried out with a catalyst, before an exchange is necessary.

Preferably, the run time $\Delta t(i)$ is more than 100 h, preferably more than 200 h, further preferably more than 500 h, and particularly preferably more than 1000 h.

Accordingly, the present invention also relates to a process as described above, wherein the run time $\Delta t(i)$ is at least 100 h.

During the contacting according to (i), the catalyst, as described above, is additionally contacted at least once with a mixture G2 comprising ethanol for a run time $\Delta t(ii)$. This contacting proceeds preferably to a time point at which deactivation or partial deactivation of the catalyst has already begun.

The contacting with the ethanol-comprising mixture according to (ii), in the process according to the invention, is not carried out during the entire run time $\Delta t(i)$ but only for one or more restricted time periods $\Delta t(ii)$ during the run time $\Delta t(i)$. Preferably, the run time $\Delta t(ii)$ is less than 24 h. Further preferably, the run time $\Delta t(ii)$ is in the range from 0.1 to 12 h, preferably in the range from 0.1 to 6 h, further preferably in the range from 0.1 to 5 h, and particularly preferably in the range from 0.1 to 4 h.

Accordingly, the present invention also relates to a process as described above, wherein the run time $\Delta t(ii)$ is in the range from 0.1 to 4 h.

Depending on requirements, during the run time $\Delta t(i)$, the contacting according to (ii) can be carried out once or a plurality of times, for example five times, four times, three times, twice or once. How often step (ii) is carried out is dependent, for example, on the degree of deactivation of the catalyst or on the length of the run time $\Delta t(i)$. In the event that the contacting according to (ii) is carried out not only once, but a plurality of times, the sum of all run times $\Delta t(ii)$ is likewise less than $\Delta t(i)$. Preferably, the ratio of $\Delta t(i)$ to the sum of the run times $\Delta t(ii)$, that is to say to $\Sigma(\Delta t(ii))$, is in the range from 10 to 10000, such as in the range from 100 to 10 000, preferably in the range from 10 to 1000.

In addition, the run time $\Delta t(ii)$, in the case of repeated contacting, can, according to requirements, vary in the above-mentioned range, i.e. should the catalyst be contacted more than once with the mixture G2 each time for a run time Δt(ii), from time to time Δt(ii) can be varied within the abovementioned ranges.

For the contacting according to (ii), the mixture G2 is preferably fed together with the mixture G1 into the at least one reactor and there brought into contact with the catalyst as described above. In this case, G1 and G2 can be fed into the at least one reactor at various sites or together at the same position. Preferably, the mixture G2, before it is fed in, is mixed with G1, i.e. preferably added to the mixture G1, and the resultant mixture of G1 and G2 is then passed as feed gas into the at least one reactor.

Accordingly, the present invention also relates to a process, as described above, wherein the mixture G2, before the contacting with the catalyst according to (ii), is added to the mixture G1.

The contacting according to (ii) for the run time Δt(ii) is here carried out essentially at the same conditions as the contacting according to (i), i.e. at temperatures in the range from 180° C. to 300° C., preferably at temperatures in the range from 185° C. to 290° C., further preferably temperatures in the range from 190° C. to 280° C., and particularly preferably temperatures in the range from 200° C. to 270° C. Preferably, the mixture G2, before it is added to G1, is brought to a temperature in the range from 170 to 270° C.

Further preferably, the contacting proceeds at a pressure in the range from 5 bar to 30 bar, preferably at a pressure in the range from 10 bar to 20 bar, and particularly preferably at a pressure in the range from 14 bar to 20 bar. In addition, the contacting according to (ii) for the run time Δt(ii) is carried out essentially at the same GHSV as the contacting according to (i), i.e., that is to say a GHSV in the range from 800 to 10 000 per hour, preferably in the range from 2000 to 6000, further preferably in the range from 3000 to 6000.

As far as the composition of the mixture G2 is concerned, this mixture comprises ethanol, preferably in an amount of at least 0.01%, based on the total weight of G2. Preferably, the mixture comprises ethanol. "Comprise ethanol", in this context, means that G2 comprises ethanol plus the customary impurities present in ethanol, such as, for example, methanol, propanol, acetaldehyde and/or acetic acid. The ethanol used in (ii), according to one embodiment of the invention, is ethanol which is unreacted in the dehydration of ethanol according to (a) and is purified in a suitable manner.

According to an alternative embodiment, the mixture G2, in addition to ethanol, comprises at least one evaporable promoter selected from the group consisting of Re, W, and Mo. The expression "evaporable promoter" as used in the context of the invention comprises not only evaporable compounds of the promoters but also gas streams comprising the promoter in its elemental form or in a suitable, i.e. evaporable or volatile, form.

If the at least one evaporable promoter is rhenium, the rhenium is preferably used as rhenium compound, further preferably as ethanolic solution of a rhenium compound. Rhenium heptoxide, ammonium perrhenate or methyltrioxorhenium are preferably used as rhenium compound.

Accordingly, the present invention also relates to a process as described above, wherein the mixture G2 additionally comprises rhenium heptoxide.

In the event that G2, in addition to ethanol, comprises at least one evaporable promoter, G2 comprises the at least one promoter preferably in an amount in the range from 10 to 2000 ppm, preferably in an amount in the range from 50 to 500 ppm, based on the total weight of the catalyst used.

The mixture G2, during the run time Δt(ii), is preferably used in an amount in the range from 0.01% by volume to 5% by volume, further preferably an amount in the range from 0.01 to 3% by volume, further preferably an amount in the range from 0.01 to 2% by volume, further preferably an amount in the range from 0.01 to 1% by volume, further preferably an amount in the range from 0.01 to 0.5% by volume, based on the total volume of G1 and G2.

Accordingly, the present invention also relates to a process as described above, wherein the mixture G2, during the run time Δt(ii), is used in an amount in the range from 0.01 to 0.5% by volume, based on the sum of the volumes of G1 and G2.

If the contacting according to (ii) is carried out at least two times, the steps (ii) carried out each time can be carried out essentially under the same process conditions, that is to say, for example, having essentially the same composition of the mixture G2, having essentially the same amount of G2, based on the sum of the volumes of G1 and G2, essentially the same run time Δt(ii), at essentially the same temperature and essentially the same pressure. Likewise, it is possible that the at least two steps (ii) differ in one or more parameters such as, for example, the composition of the mixture G2, the amount of the mixture G2 used, the temperature, the pressure and/or the run time Δt(ii).

In the event that, for example, the composition of the mixture G2, as described above, is varied, the catalyst, for example, during the run time Δt(iix) is brought into contact with a mixture G2 and during the run time Δt(iiy) is brought into contact with a further mixture G2 which differs in its composition, i.e., for example, in the number and/or amount of the evaporable promoters if appropriate comprised therein, from the mixture G2 which is used during the run time Δt(iix).

According to one embodiment of the process according to the invention, the catalyst is contacted according to (ii) at least once with a mixture G2 which comprises ethanol and at least once with a mixture G2 comprising ethanol and rhenium.

If the contacting is carried out at least two times, the respective treatments according to (ii) can be carried out in time directly one after the other. Likewise, it is possible that the individual steps (ii) are performed staggered in time with respect to one another. If the contacting according to (ii) is carried out at least three times, the time intervals between the respective steps (ii) can be the same or different. Likewise, it is possible to carry out two or more steps (ii) directly subsequently to one another, i.e. without a time interval, and two or more steps with a time interval.

Advantageously, the process according to the invention is carried out in a cyclic process. In this case the mixture G1 is recirculated through the reactor and so brought into contact with the catalyst according to (i). At defined time points, as described above, additionally at least once, for a period Δt(ii), G2 is passed together with G1 through the reactor. After the contacting, the ethylene oxide formed by the direct oxidation and also the byproducts formed in the reaction are removed from the product gas stream. For example, at least a part of the carbon dioxide present in the product mixture is removed. This removal proceeds, typically, by means of a carbon dioxide absorber. If the product mixture also comprises ethanol as a result of the contacting according to (ii), this is, if appropriate, likewise removed in a suitable manner. The removal proceeds typically by gas scrubbing and/or a condenser, wherein the ethanol is absorbed or condensed out. The ethylene oxide can be removed from the product gas stream and its workup can proceed according to the conventional processes of the prior art (cf. Ullmann's Encyclopedia of Industrial Chemistry; 5th Ed.; vol. A2 0; pp. 117-135, 123-125; VCH Verlagsgesellschaft; Weinheim 1987). The mixture obtained after removing the byproducts and ethylene oxide and/or if appropriate ethanol, after supplementation with the required amounts of ethylene, oxygen, and optionally further components, is again passed into the reactor as mixture G1 which comprises the above described components.

The invention will be described in more detail by the examples hereinafter.

EXAMPLES

The examples were carried out in an experimental reactor comprising a vertically upright reaction tube made of stainless steel having an inner diameter of 6 mm and a length of 2300 mm. The reaction tube which was provided with a jacket was heated with hot oil of temperature T which flowed through the jacket. To a very good approximation the temperature of the oil corresponds to the temperature in the reaction tube and therefore the reaction temperature. The reaction tube was packed from bottom to top to a height of approximately 200 mm with inert steatite balls, thereabove to a height of approximately 1100 mm with catalyst chips of particle size 0.5-1.0 mm and thereabove to a height of approximately 700 mm with inert steatite balls. The feed gas entered into the reactor from the top and exited again at the lower end after passing through the catalyst bed.

The feed gas comprised 7% by volume of $O_2$ and 35% by volume of $C_2H_4$ and also 0.15% by volume of $H_2O$, 1.0% by volume of $CO_2$, remainder $CH_4$ (methane). The experiments were carried out at p=15 bar, a gas hourly space velocity (GHSV) of 4750 h−1 and also a space-time yield of ethylene oxide of 0.25 kgEO/L of cat./h.

The reaction temperature was controlled in accordance with the predetermined ethylene oxide space-time yield. For optimization of the catalyst with respect to selectivity and conversion rate, 3 ppm by volume of ethyl chloride were added as moderator to the feed.

The gas exiting at the reactor outlet was analyzed gas chromatographically by means of online GC. From the analytical results, the conversion rate (catalyst activity) and selectivity were determined. At a predetermined ethylene oxide space-time yield, the reaction temperature necessary therefor was a measure of the catalyst activity, wherein the catalyst activity in this case is inversely proportional to the reaction temperature.

A higher catalyst activity, accordingly, becomes clear owing to a lower reaction temperature at a predetermined ethylene oxide space-time yield. A lower catalyst activity, conversely, becomes clear via a higher reaction temperature at a predetermined ethylene oxide space-time yield.

The silver catalyst used comprised approximately 15% by weight of silver on a support material of alpha-$Al_2O_3$ having small fractions of $SiO_2$ and also traces of alkali metal oxides and alkaline earth metal oxides (specific water absorption approximately 0.5 ml/g; specific BET surface area of approximately 0.9 m²/g measured as specified in DIN-ISO 9277). As selectivity-increasing promoter elements, the catalyst additionally comprised lithium and cesium and also tungsten and sulfur.

The metering of the alcohols in liquid form was performed by means of an HPLC pump (Bischoff type with micropump head 0-2 ml) at reaction pressure. The alcohols in this case were metered into the feed gas stream above the actual reaction tube and heated to 175° C. within an approximately 1000 mm long stainless steel tube coil heated to approximately 175° C. The alcohols in this case, depending on their boiling temperature, were vaporized (in the case of methanol and ethanol) or preheated in liquid form (in the case of 1-butanol, 1-propanol and 2-propanol).

Example 1

Feeding in Ethanol

The silver catalyst was installed into the reaction tube as described. First, the catalyst was flushed for a period of approximately 12 h with nitrogen unpressurized at 230° C. corresponding to a GHSV of approximately 3000 h−1 and thus freed from moisture or other adhering substances. The catalyst was started up after reaching the reaction pressure of 15 bar by stepwise adjustment of the above described feed gas mixture, wherein the nitrogen was replaced stepwise as inert gas by methane. Then the reaction temperature was adjusted in such a manner that a space-time yield of ethylene oxide of 0.25 kg(EO)/l(cat.)/h was achieved.

The catalyst, after approximately 150 h of operating time, reached a steady state, i.e. a constant level of activity and selectivity. Then ethanol was fed in without the remaining reaction conditions being altered. The metering rate was 2.0 ml/h, corresponding to 0.3% by volume of ethanol. In the course of 60 min., an ethanol amount of 2 ml was added. Immediately after the addition, a decrease in catalyst performance occurred. After some hours of operating time, again a steady state performance level of the catalyst at a predetermined ethylene oxide space-time yield was achieved. The results are summarized in table 1.

TABLE 1

Catalyst performance before, during and after feeding in ethanol

| Comment | Run time (h) | Temperature T (° C.)* | Selectivity (%) |
|---|---|---|---|
| Steady state before feed | 120 | 229 | 81.4 |
| Immediately after feed | — | 229 | 78.9 |
| Steady state after feed | 140 | 228 | 81.7 |

*The temperature is inversely proportional to the catalyst activity.

Example 2

Comparative Example

Feeding in Methanol

Example 2 was carried out similarly to example 1, but with the difference that instead of the feeding in of ethanol, methanol was fed in. The results are summarized in table 2.

TABLE 2

Catalyst performance before, during and after feeding in methanol

| Comment | Run time (h) | Temperature (° C.)* | Selectivity (%) |
|---|---|---|---|
| Steady state before feed | 120 | 248 | 81.8 |
| Immediately after feed | — | 248 | 80.7 |
| Steady state after feed | 150 | 248 | 82.0 |

*The temperature is inversely proportional to the catalyst activity.

Example 3

Comparative Example

Feeding in 1-propanol

Example 3 was carried out in a similar manner to example 1, but with the difference that instead of feeding in ethanol, 1-propanol was fed in. The results are summarized in table 3.

TABLE 3

Catalyst performance before, during and after feeding in 1-propanol

| Comment | Run time (h) | Temperature (° C.)* | Selectivity (%) |
|---|---|---|---|
| Steady state before feed | 160 | 228 | 81.5 |
| Immediately after feed | — | 228 | 80.1 |
| Steady state after feed | 200 | 228 | 81.3 |

*The temperature is inversely proportional to the catalyst activity.

Example 4

Comparative Example

Feeding in 2-propanol

Example 4 was carried out in a similar manner to example 1, but with the difference that, instead of feeding in ethanol, 2-propanol was fed in. The results are summarized in table 4.

TABLE 4

Catalyst performance before, during and after feeding in 2-propanol

| Comment | Run time (h) | Temperature (° C.)* | Selectivity (%) |
|---|---|---|---|
| Steady state before feed | 190 | 229 | 82.0 |
| Immediately after feed | — | 229 | 80.2 |
| Steady state after feed | 200 | 230 | 82.0 |

*The temperature is inversely proportional to the catalyst activity.

Example 5

Comparative Example

Feeding in 1-butanol

Example 5 was carried out in a similar manner to example 1, but with the difference that, instead of feeding in ethanol, 1-butanol was fed in. The results are summarized in table 5.

TABLE 5

Catalyst performance before, during and after feeding in 1-butanol

| Comment | Run time (h) | Temperature (° C.)* | Selectivity (%) |
|---|---|---|---|
| Steady state before feed | 170 | 226 | 81.6 |
| Immediately after feed | — | 226 | 80.5 |
| Steady state after feed | 190 | 226 | 81.9 |

*The temperature is inversely proportional to the catalyst activity.

Example 6

Comparative Example

No Alcohol Fed in

Example 6 was carried out in a similar manner to example 1, but with the difference that no alcohol was fed in. The results are summarized in table 6.

TABLE 6

Catalyst performance at defined run times without an alcohol fed in

| Comment | Run time (h) | Temperature (° C.)* | Selectivity (%) |
|---|---|---|---|
| Steady state | 125 | 228 | 81.4 |
| Steady state | 250 | 228 | 81.4 |

*The temperature is inversely proportional to the catalyst activity.

It may be seen that using the process according to the invention the activity, which is inversely proportional to the reaction temperature, and the selectivity of the silver catalyst are affected. It is therefore possible in the case of the catalysts treated according to the invention to lower the reaction temperature after the treatment for the same space-time yield. This is also advantageous to the extent that using a low reaction temperature the formation of unwanted byproducts decreases. As can be seen from the examples, in example 1 according to the invention, after treatment a decrease in reaction temperature (for the same space-time yield) and an increase in selectivity are achieved. In none of the comparative experiments in which the process was carried out using alcohols different from ethanol could such a decrease in reaction temperature (for the same space-time yield) be achieved.

The invention claimed is:

1. A continuous process for producing an alkylene oxide by direct oxidation of an alkene with oxygen, which comprises
    (i) continuous contacting of a silver-comprising catalyst with a mixture G1 comprising the alkene and oxygen for a run time $\Delta t(i)$;
    (ii) contacting at least once the catalyst according to (i) during the continuous contacting according to (i) with an additional mixture G2 comprising ethanol for a run time $\Delta t(ii)$,
    wherein $\Delta t(i) > \Delta t(ii)$.

2. The process according to claim 1, wherein the run time $\Delta t(i)$ is at least 100 h.

3. The process according to claim 1, wherein the run time $\Delta t(ii)$ is in the range from 0.1 to 4 h.

4. The process according to claim 1, wherein the contacting according to (i) proceeds at a temperature in the range from 180° C. to 300° C.

5. The process according to claim 1, wherein the contacting according to (i) proceeds at a pressure in the range from 14 bar to 20 bar.

6. The process according to claim 1, wherein the contacting according to (i) proceeds with a gas hourly space velocity (GHSV) in the range from 3000 to 6000 $h^{-1}$.

7. The process according to claim 1, wherein the mixture G2, before the contacting with the catalyst according to (ii), is added to the mixture G1.

8. The process according to claim 7, wherein the mixture G2 is brought to a temperature in the range from 170 to 270° C. before the addition.

9. The process according to claim 1, wherein the mixture G2 is used in an amount in the range from 0.05% by volume to 1% by volume, based on the sum of the volumes of G1 and G2.

10. The process according to claim 1, wherein the alkene is ethylene and the alkylene oxide is ethylene oxide.

11. The process according to claim 1, wherein the mixture G1 comprises an inert gas.

12. The process according to claim 11, wherein the inert gas is selected from the group consisting of nitrogen, argon, methane, helium and mixtures of two or more thereof.

13. The process according to claim 1, wherein the mixture G1 comprises a halogen compound.

14. The process according to claim 1, wherein the mixture G1 additionally comprises a nitrogen compound.

15. The process according to claim 14, wherein the nitrogen compound is nitrogen monoxide or nitrogen dioxide or a mixture thereof.

16. The process according to claim 1, wherein the mixture G2 additionally comprises rhenium heptoxide.

17. The process according to claim 1, wherein the silver-comprising catalyst comprises an inert support material.

18. The process according to claim 1, wherein the catalyst comprises silver in an amount of 10 to 30% by weight, based on the total weight of the catalyst.

19. The process according to claim 1, wherein the catalyst additionally comprises at least one promoter.

20. The process according to claim 19, wherein the at least one promoter is selected from the group consisting of Re, W, Mo, Rb, Li, K, Cs, Sr, Ba, Ca, P, B, In, Sn, Sb, Tl, Pb, S, Bi and mixtures of two or more thereof.

* * * * *